United States Patent [19]

Gibson

[11] Patent Number: 5,787,879
[45] Date of Patent: Aug. 4, 1998

[54] METHOD OF ADMINISTERING OXYGEN TO A PATIENT AFTER GENERAL ANESTHESIA USING A PARTICULAR ADAPTER

[76] Inventor: William Patrick Gibson, 446 N. Geyer Rd., Kirkwood, Mo. 63112

[21] Appl. No.: 615,502

[22] Filed: Mar. 12, 1996

[51] Int. Cl.$^6$ ............................................. A61M 16/00
[52] U.S. Cl. ........................... 128/202.27; 128/204.18; 128/912; 128/DIG. 26
[58] Field of Search .................. 128/202.27, DIG. 26, 128/912, 204.18, 207.14, 207.17; 604/283, 905; 285/351, 177

[56] References Cited

U.S. PATENT DOCUMENTS

| | | | |
|---|---|---|---|
| 3,817,561 | 6/1974 | Kay | 285/177 |
| 4,014,326 | 3/1977 | Müller | 128/204.25 |
| 4,969,879 | 11/1990 | Lichte | 604/283 |
| 4,991,576 | 2/1991 | Henkin et al. | 128/202.27 |
| 5,193,633 | 3/1993 | Ezenwa | 180/65.1 |
| 5,370,111 | 12/1994 | Reeder et al. | 128/204.18 |
| 5,399,173 | 3/1995 | Parks et al. | 285/177 |
| 5,497,766 | 3/1996 | Foster et al. | 128/204.18 |

*Primary Examiner*—Aaron J. Lewis
*Assistant Examiner*—William J. Deane, Jr.
*Attorney, Agent, or Firm*—Stephen C. Shear

[57] ABSTRACT

A surgical procedure done under general anesthesia in which a patient is first operated on in an operating room and thereafter moved from the operating room to a recovery room is disclosed herein. During general anesthesia the patient is administered oxygen from a first oxygen source through a cooperating tube disengagably connected at a first end to the source and at a second opposite end to a mask or endotracheal tube attached to the patient in a way that allows the patient to receive oxygen from the source. After surgery, while being moved from the operating room to a recovery room, the patient is administered oxygen from a second, portable source using the very same cooperating tube. Specifically, after the patient has begun spontaneous ventilation, the first end of the cooperating tube is disconnected from the original oxygen source and reconnected to the portable source. At the same time, the mask or endotracheal tube remains attached to the patient and the patient is thereafter moved along with the portable oxygen source and the cooperating tube to the recovery room. In order to accommodate the switching of the cooperating tube from the original oxygen source to the portable source, a specifically designed adapter is utilized.

9 Claims, 2 Drawing Sheets

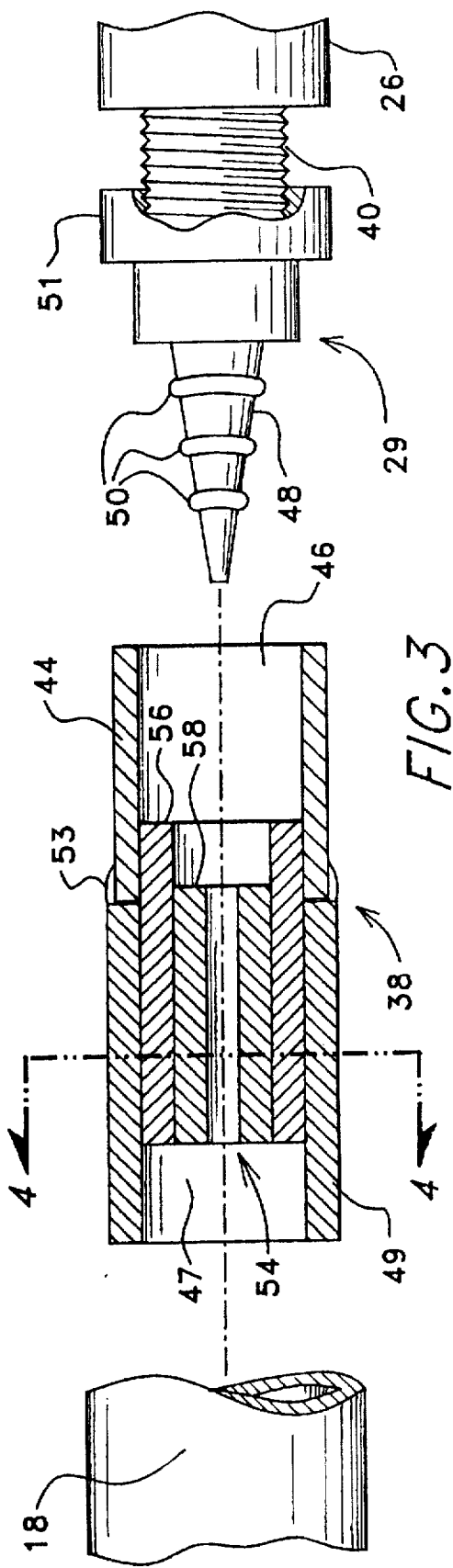

METHOD OF ADMINISTERING OXYGEN TO A PATIENT AFTER GENERAL ANESTHESIA USING A PARTICULAR ADAPTER

BACKGROUND OF THE INVENTION

The present invention relates generally to techniques for administering oxygen and more particularly to a method of administering oxygen to a patient after general anesthesia and to a specific adapter for use in carrying out the method.

The heretofore typical way of administering oxygen during and after general anesthesia is illustrated in FIGS. 1A to 1C. In FIG. 1A, a patient 10 is shown on an operating table 12 being administered oxygen and anesthesia from sources generally indicated at 14. To this end, a conventional mask or endotracheal tube generally indicated at 16 is operatively positioned over the face of the patient or in the trachea and connected to the oxygen/anesthesia sources 14 through oxygen and anesthesia tubes 18 and 20 which are connected in the conventional method.

When patient 10 is spontaneously ventilating, he or she is transferred to a mobile transport bed 22, as illustrated in FIG. 1B. At approximately the same time, the original mask or endotracheal tube 16 is replaced with a second mask or nasal prong device 24 which is connected to a portable source of oxygen 26 through a second cooperating tube 28. Tube 28 is usually connected to portable source 26 by means of an available tube connector 29. Portable oxygen source 26 is mounted to the mobile bed 22 by suitable, readily providable means 31 and the patient is moved from the operating room to the recovery room and, at the same time, he or she is administered oxygen.

Upon reaching the recovery room, the patient is left on the mobile bed as illustrated in FIG. 1C. In the recovery room, second mask or nasal prong device 24 is removed from the patient and replaced with a third mask 32 which is connected to a wall mounted oxygen source 34 through still another cooperating tube 36.

The procedure described above assumes of course that the patient requires oxygen immediately after general anesthesia and specifically as he or she is being transported from the operating room to the recovery room and thereafter at least for a short period of time. It is not suggested here that all patients require post-operative oxygen. However, when it is necessary, the above described procedure illustrates the typical way in which it has been carried out heretofore. Note specifically that this procedure may require three different masks or nasal prong devices and three different cooperating oxygen tubes. Not only it is wasteful using multiple masks or nasal tube devices and tubes both from a cost standpoint and from an environment standpoint, but it is also cumbersome and time consuming to have to change these components from one procedural step to the next. As will be seen hereinafter, the present invention overcomes these drawbacks in a very simple and economical manner.

SUMMARY OF THE INVENTION

As will be described in more detail hereinafter, there is disclosed herein a surgical procedure in which a patient is first given general anesthesia in an operating room and thereafter moved from the operating room to a recovery room. During general anesthesia the patient is administered oxygen from a first oxygen source through a cooperating tube disengagably connected at a first end to the source and at a second opposite end to a mask or endotracheal tube attached to the patient in a way which allows the patient to receive oxygen from the source.

In accordance with one aspect of the present invention, a specific method of administering oxygen to the patient after general anesthesia using the same portable oxygen source recited above and the first-mentioned tube is also disclosed herein. When the patient is spontaneously ventilating, the first end of the first cooperating oxygen tube is disconnected from the original oxygen source and reconnected to the portable source. With the mask attached to the patient, the patient is moved along with the portable oxygen source, the cooperating tube and the mask to the recovery room while, at the same time, oxygen is administered to him or her from the portable oxygen source through the cooperating tube and mask. Thus, in accordance with this aspect of the present invention, the same mask is used during surgery and immediately thereafter, i.e. it does not have to been removed, and the same cooperating oxygen tube is used.

In accordance with a second aspect of the present invention, after the patient has reached the recovery room, the first end of the cooperating oxygen tube is disconnected from the portable oxygen supply and is reconnected to a wall mounted supply of oxygen. In addition, the second end of the cooperating tube is disconnected from the original mask and reconnected to a different mask-type device for use by the patient. Thus, throughout the entire surgical and post surgical procedure, one and only one cooperating oxygen tube is utilized.

In disconnecting the cooperating oxygen tube from the first oxygen source and reconnecting it to the portable source of oxygen, a separate adapter is utilized. The portable oxygen source typically includes an externally threaded tube connecting output having thread mounted thereon the previously mentioned connector 29. In accordance with a third aspect of the present invention, the adapter utilized is configured to readily connect the cooperating oxygen tube to either the tube connecting output of the portable oxygen source or to the connector 29 since the connector is not always on the tube connecting output. In an actual embodiment, as will be seen, the adapter includes an arrangement of at least two concentric tubes opened at corresponding first and second ends. At least the first ends of these tubes are successively displaced axially deeper into the arrangement starting with outermost tube such that the first end of the innermost tube is disposed most deeply within the arrangement of tubes. In this way, as will also been seen, the adapter is configured to accommodate both the connector 29 and the tube connecting output of the portable oxygen source without the connector.

DESCRIPTION OF THE DRAWINGS

The various aspects of the present invention, as summarily recited above, will be described in more detail hereinafter in conjunction with the drawings, wherein:

FIGS. 2A, 2B, and 2C diagrammatically depict the way in which a patient is administered oxygen in accordance with the present invention, first during general anesthesia in the operating room (FIG. 2A), then immediately thereafter during transport to the recovery room (FIG. 2B), and finally upon reaching the recovery room (FIG. 2C);

FIG. 3 diagrammatically depicts in partially broken away perspective view and partially in longitudinal sectional view an adapter, an oxygen tube and part of a portable oxygen source which are utilized in the procedure of administering a patient oxygen, as depicted in FIGS. 2A–C; and FIG. 4 is a cross-sectional illustration in longitudinal sectional view, of the adapter of FIG. 3 taken generally along line 4—4 in FIG. 3.

DETAILED DESCRIPTION

Figure 1A:
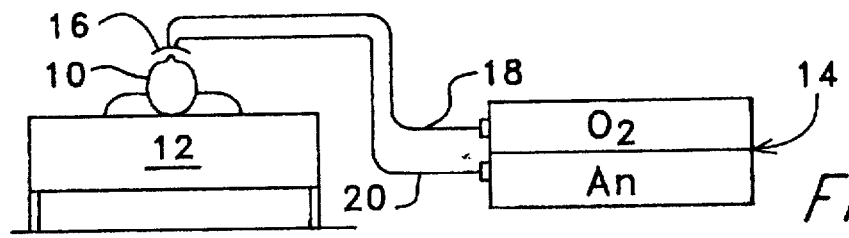
FIGS. 1A, 1B, and 1C diagrammatically depict a typical prior art procedure showing the way in which a patient is administered oxygen (1) during general anesthesia (FIG. 1A), (2) immediately thereafter on the way to the recovery room (FIG. 1B), and upon reaching the recovery room (FIG. 1C)
Figure 1B:
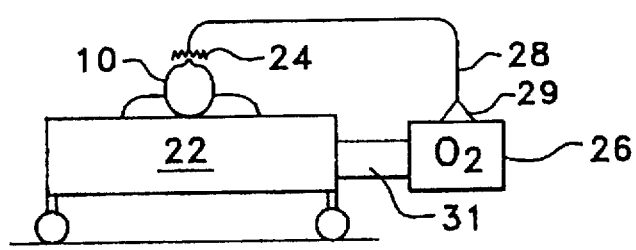
Figure 1C:
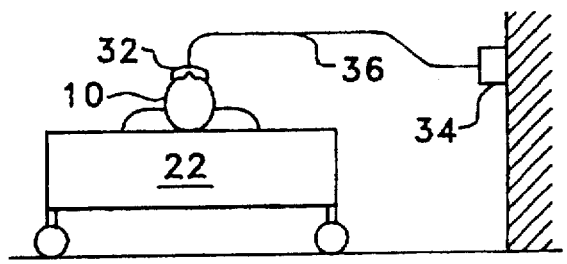
Figure 2A:
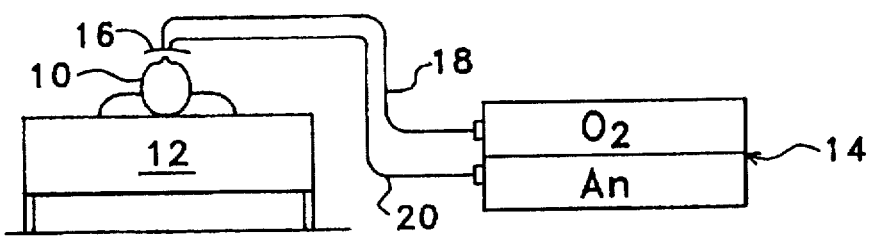
Figure 2B:
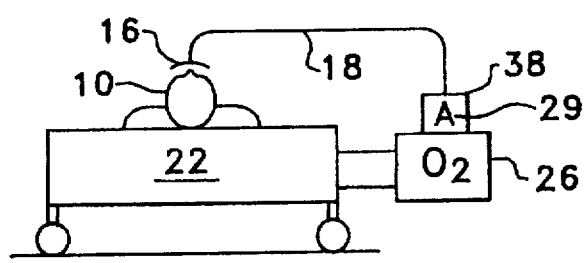

Turning now to the drawings, wherein like components are designated by like reference numerals throughout the various figures, attention is immediately directed to FIGS. 2A, 2B, and 2C, in as much as FIGS. 1A, 1B, and 1C were discussed previously. FIG. 2A depicts the same patient 10 on operating table 12 during general anesthesia. Patient 10 is shown being administered oxygen and anesthesia from oxygen/anesthesia sources 14 through cooperating tubes 18 and 20 and mask or endotracheal tube 16. Indeed, FIG. 2A may be identical to previously described prior art FIG. 1A. That is to say, during general anesthesia, there may be no difference in the way in which patient 10 is administered oxygen in accordance with the prior art and the way he or she is administered oxygen in accordance with the present invention.

However, unlike the prior art approach described previously, the present invention continues to utilize the same cooperating oxygen tube 18 to administer oxygen to patient 10 throughout the post-surgical procedures, that is, during the time the patient is transported from the operating room to the recovery room and while the patient is recovering, of course assuming he or she even requires post-surgical oxygen. In the case of the present invention and in contrast with the prior art approach described above, original mask or endotracheal tube 16 may remain operatively attached to the patient after general anesthesia. In this case, the cooperating anesthesia tube 20 is disconnected from the mask or endotracheal tube while, at the same time, the corresponding end of cooperating oxygen tube 18 remains in its connected position to the mask. However, the opposite end of oxygen tube 18 is disconnected from its original oxygen source and reconnected to portable oxygen source 26 which is mounted to transport bed 22 in the manner described previously.

As will be described in detail hereinafter in conjunction with FIGS. 3 and 4 and in accordance with the present invention, a newly configured adapter 38 is provided to connect the otherwise free end of oxygen tube 18 to either previously described connector 29 or to the tube connecting output forming part of the overall portable oxygen source, depending on whether the connector 29 is present. In this way, the patient can be moved along with the portable oxygen source, the cooperating tube and the mask to the recovery room while, at the same time, oxygen is being administered from the portable oxygen source through the tube and mask.

Once patient 10 reaches the recovery room, he or she remains in the portable transport bed. If it is necessary to continue administering oxygen to patient 10, original tube 18 is disconnected from portable source 26 at the end of the tube including adapter 38 and it is reconnected to wall-hung oxygen source 34. In this case, since previously described recovery room oxygen tube 36 is typically identical to original oxygen tube 18, the latter tube is readily connectable to the wall-hung oxygen source 34 without the need for adapter 38 or any other such adapter. At the same time, tube 18 is readily disconnected from original mask 16 and reconnected to the new mask, for example the previously described recovery room mask 32 or other special mask-like devices, as illustrated in FIG. 2C.

There are a number of advantages to the oxygen administering procedure described immediately above in conjunction 2A, 2B and 2C. First, because neither the original mask or endotracheal tube nor the original oxygen tube has to be replaced immediately after general anesthesia and during patient transport from the operating room to the recovery room, the transport of patient with oxygen administration will go faster. The end of tube 18 will be removed from the anesthesia machine and the adapter applied and attached to portable oxygen source. Tube 20 will be disconnected from the mask or endotracheal tube 16. No other additional mask and tubes will have to be stocked in the operating room. No one will have to leave the operating room to obtain the transport mask and tubes. In the recovery room, there will be fewer needs for oxygen tubing 36. This will decrease the need for a local storage area and stocking time will be decreased. Additionally, because the same oxygen tube is used throughout the entire procedure, less tubes are used which not only translates to economic savings but also to environmental savings.

Turning now to FIG. 3, attention is directed specifically to previously recited adapter 38 which is shown in longitudinal section in combination with a portion of previously described oxygen tube 18, connector 29 and the tube connecting output of portable oxygen source 26. The tube connecting output which is indicated at 40 is an externally threaded tubular extension of oxygen source 26. As illustrated best in FIG. 3, connector 29 includes an outwardly projecting, generally cone shaped portion 48 which carries a series of outwardly, axially spaced angular ribs 50. The back end 51 of the connector is internally threaded so as to thread mount onto tube connecting output 40.

Still referring to FIGS. 3 and 4, adapter 38 is shown including two outer tubes 44 and 49 having slightly different outer diameters and positioned against one another in end-to-end relationship and bonded together in this position by suitable bonding substance 53. At the same time, they are bridged together internally by a tube 56. Tube 49 has open end 47 and tube 44 has open end 46. Open end 46 is configured to receive tube connecting output 40 (without the connector 29 mounted thereon) in a gas sealed, friction tight manner. Tube 49 at open end 47 is configured to receive the free end of tube 18 on it's outer surface.

Adapter 38 also includes an arrangement 54 of additional concentric tubes, the previously recited bridge tube 56 and a second tube 58 disposed within outermost tubes 44 and 49. These latter tubes which are preferentially constructed of a relatively soft, deformable substance, for example rubber or a soft plastic, are opened at corresponding first ends which face opening 46 and corresponding second ends which face opening 47. As seen best in FIG. 3, at least the ends of tubes 56 and 58 that face opening 46 are successively displaced axially deeper into the arrangement starting with the outermost tube 56 such that the corresponding end of the innermost tube 58 is disposed most deeply within outermost tube 44 with respect to end 46. In this way, if the connector 29 is mounted on output 40 of oxygen source 26, as the portion 48 of connector 29 is inserted into the adapter 38, at least a segment of portion 48 will engage in a gas sealed, friction tight manner with one of the inner tubes.

While adapter 38 is provided as a preferred way to interconnect tube 18 with portable oxygen source 26, the present invention is not limited to the particular adapter described and, indeed, it is within the scope of the present invention to provide a tube 18 and an oxygen source 26 which are custom designed to interconnect to one another without the use of any adapters whatsoever or with different types of adapters than one described herein. In addition, adapter 38, as described is preferably constructed of a flexible or deformable material such as rubber or plastic, but could be made of any suitable material so long as it functions in the manner described.

What is claimed is:

1. In a procedure in which a patient is administered a general anesthesia in an operating room and thereafter moved from the operating room to a recovery room, comprising the steps of providing a first source of oxygen and a source of anesthesia; providing a mask or endotracheal tube and attaching at least one of said mask or endotracheal tube to the patient; providing oxygen and anesthesia to a patient from the first oxygen source; providing a cooperating tube disengagably connected at a first end to the first source of oxygen and at a second opposite end to the mask or endotracheal tube attached to the patient in a way that allows the patient receive oxygen from the first source, said method further comprising:

(a) providing a second, portable source of oxygen, said second portable oxygen source including a tube connecting output and a separate connector configured to disengagably mount onto said tube connecting output;

(b) providing an adapter having one section thereof designed in a way to connect directly to the tube connecting output of said portable oxygen source and having a second section thereof which is designed in a way to connect directly to said connector when the latter is mounted on said output;

(c) responsive to the patient's spontaneous ventilation, disconnecting the first end of said cooperating tube from said first oxygen source, reconnecting said first end to said adapter and connecting the adapter to said portable source (I) by connecting said adapter directly to the tube connecting output of said portable oxygen source when the connector is not being used and (ii) by connecting said adapter to the connector when the connector is mounted on said output; and (d) maintaining the mask or endotracheal tube attached to the patient, moving the patient along with the second portable oxygen source, the cooperating tube and the mask or endotracheal tube to the recovery room while at the same time administering oxygen to the patient from the second portable oxygen source through the cooperating tube and mask or endotracheal tube.

2. A method according to claim 1 including the steps of:

(d) disconnecting the first end of said cooperating tube from said portable oxygen supply when the patient reaches the recovery room and reconnecting it to a wall mounted supply of oxygen; and (e) disconnecting the second end of the cooperating tube from the mask or endotracheal and reconnecting it to a different device for use by the patient.

3. A method according to claim 1 wherein said adapter includes an arrangement of at least two concentric tubes opened at corresponding first and second ends, at least said first ends of said tubes being successively displaced axially deeper into the arrangement starting with the outermost tube such that the first end of the innermost tube is disposed most deeply within the arrangement of tubes.

4. A method according to claim 3 wherein said adapter includes an outermost tube configured to receive in a gas sealed, friction tight manner the tube connecting output of said oxygen source directly and a plurality of concentric inner tubes configured such that one thereof will receive in a gas sealed, friction manner said connector if the latter is mounted on said output.

5. In a tube connecting arrangement for connecting a tube to a portable source of oxygen for use in a procedure in which a patient is administered general anesthesia in an operating room and thereafter moved from the operating room to a recovery room, wherein during general anesthesia the patient is administered oxygen from a first oxygen source through a cooperating tube disengagably connected at a first end to the source and at a second opposite end to a mask or endotracheal tube attached to the patient in a way that allows the patient to receive oxygen from the source, wherein after surgery the patient may also be administered oxygen as he or she is moved to the recovery room in which case the first end of said tube is disconnected from the first oxygen source and reconnected to said portable source of oxygen, and wherein said connecting arrangement includes a tube connecting output forming part of said portable oxygen source and a connector configured to disengageably mount onto said tube connecting output, the improvement comprising an adapter for connecting the first end of said tube to the tube connecting output of said portable oxygen source when the connector is not mounted on the output and to said connector when the latter is mounted on said tube connecting output, said adapter including:

(a) a main body having opposite first and second ends;

(b) a first segment forming part of said main body for connecting the first end of said main body to the first end of said tube; and (c) a second segment forming part of said main body and having a first section designed in a way to connect said main body directly to the tube connecting output of said portable oxygen source when the connector is not mounted on the output and having a second section designed in a to connect said main body to said connector when the latter is mounted on said output.

6. The improvement according to claim 5 wherein said second connecting means includes an arrangement of at least two concentric tubes opened at corresponding first and second ends, at least said first ends of said tubes being successively displaced axially deeper into the arrangement starting with the outermost tube such that the first end of the innermost tube is disposed most deeply within the arrangement of tubes.

7. The improvement according to claim 6 wherein said second connecting means includes an outermost tube configured to receive in a gas sealed, friction tight manner the tube connecting output of said oxygen source directly and a plurality of concentric inner tubes configured such that one thereof will receive in a gas sealed, friction manner said connector if the latter is mounted on said output.

8. The improvement according to claim 7 wherein said plurality of concentric inner tubes include three such tubes.

9. The improvement according to claim 7 wherein said outermost tube and said inner tubes are constructed of a deformable or flexible material.

* * * * *